United States Patent
Brooks et al.

(10) Patent No.: US 7,374,318 B2
(45) Date of Patent: May 20, 2008

(54) LIGHTED TUBING

(76) Inventors: Nancy Brooks, 6901 Roundtree, Shawnee, KS (US) 66226; James J. Brooks, 17726 W. 160th Ter., Olathe, KS (US) 66061

( * ) Notice: Subject to any disclaimer, the term of this patent is extended or adjusted under 35 U.S.C. 154(b) by 35 days.

(21) Appl. No.: 11/268,182

(22) Filed: Nov. 7, 2005

(65) Prior Publication Data

US 2007/0103926 A1     May 10, 2007

(51) Int. Cl.
  *F21V 21/08*  (2006.01)
  *F21L 4/00*  (2006.01)
  *F21S 4/00*  (2006.01)

(52) U.S. Cl. .............. 362/396; 362/572; 362/191; 362/555

(58) Field of Classification Search .............. 362/84, 362/554, 556, 800, 555, 191, 391, 227–252, 362/396, 190, 197, 199, 202, 208, 285, 288, 362/647, 652, 653, 374, 375, 418, 430, 440, 362/449, 219
See application file for complete search history.

(56) References Cited

U.S. PATENT DOCUMENTS

| | | | | |
|---|---|---|---|---|
| 3,460,541 | A * | 8/1969 | Doherty ............... | 128/207.15 |
| 4,309,743 | A * | 1/1982 | Martin ................. | 362/104 |
| 4,417,299 | A * | 11/1983 | Rupp .................. | 362/186 |
| 4,654,026 | A * | 3/1987 | Underwood .......... | 604/80 |
| 4,676,465 | A * | 6/1987 | Myotte ................ | 248/126 |
| 4,800,867 | A * | 1/1989 | Owens ................ | 126/204 |
| 4,900,314 | A * | 2/1990 | Quackenbush ....... | 604/527 |
| 5,027,741 | A | 7/1991 | Smith et al. | |
| 5,129,985 | A * | 7/1992 | Crowley ............... | 156/579 |
| 5,285,778 | A * | 2/1994 | Mackin ................ | 128/207.15 |
| 5,321,587 | A * | 6/1994 | Fujita ................... | 362/34 |
| 5,448,459 | A * | 9/1995 | Rogers ................. | 362/191 |
| 5,591,130 | A | 1/1997 | Denton | |
| 5,718,666 | A | 2/1998 | Alarcon | |
| 5,785,408 | A * | 7/1998 | Tseng .................. | 362/119 |
| 5,876,109 | A * | 3/1999 | Scalco ................. | 362/104 |
| 6,034,485 | A | 3/2000 | Para | |
| 6,050,713 | A | 4/2000 | O'Donnell et al. | |
| 6,059,768 | A * | 5/2000 | Friedman ............. | 604/523 |
| 6,074,071 | A | 6/2000 | Baumberg et al. | |
| 6,224,235 | B1 * | 5/2001 | Parker ................. | 362/190 |
| 6,257,750 | B1 | 7/2001 | Strasser et al. | |
| 6,300,722 | B1 | 10/2001 | Parra | |

(Continued)

OTHER PUBLICATIONS

UV Reactive and Glow in the Dark Heat Shrink, http://cableorganizer.com/head-shrink/, retrieved from Internet on Oct. 13, 2005.

(Continued)

*Primary Examiner*—John A. Ward
*Assistant Examiner*—David R Crowe
(74) *Attorney, Agent, or Firm*—Lathrop & Gage LC

(57) ABSTRACT

Lighted tubing includes an elongate wall and a light source. The elongate wall defines an interior channel. A conductor may be positioned adjacent to and extending from the light source to conduct light produced by the light source along the wall. A method of securing medical tubing includes the steps of providing medical tubing, providing a light source, attaching the light source to an elongate wall of the medical tubing, and the light source indicating the location of the wall in a dark environment.

26 Claims, 5 Drawing Sheets

U.S. PATENT DOCUMENTS

| | | | |
|---|---|---|---|
| 6,361,186 B1 * | 3/2002 | Slayden | 362/249 |
| 6,518,710 B1 | 2/2003 | Parra | |
| 6,694,665 B1 | 2/2004 | Moran | |
| 6,779,913 B2 * | 8/2004 | Niezrecki et al. | 362/473 |
| 6,877,877 B2 | 4/2005 | Rodriguez et al. | |
| 6,932,186 B2 * | 8/2005 | Costa et al. | 181/131 |
| 6,984,052 B1 * | 1/2006 | Del Castillo | 362/34 |
| 2002/0000720 A1 | 1/2002 | Knowles | |
| 2004/0022052 A1 | 2/2004 | Chien | |
| 2004/0196647 A1 * | 10/2004 | Palmer et al. | 362/84 |
| 2004/0210114 A1 * | 10/2004 | Simon | 600/185 |
| 2004/0236275 A1 | 11/2004 | Pruitt et al. | |
| 2005/0011282 A1 | 1/2005 | Voege et al. | |
| 2005/0065496 A1 * | 3/2005 | Simon et al. | 604/500 |
| 2005/0251119 A1 * | 11/2005 | Eaton et al. | 606/15 |
| 2006/0092620 A1 * | 5/2006 | Booty, Jr. | 362/84 |

OTHER PUBLICATIONS

GLOW, Inc., http://glowinc.com/detail.aspx?ID=1, retrieved from Internet on Oct. 13, 2005.

* cited by examiner

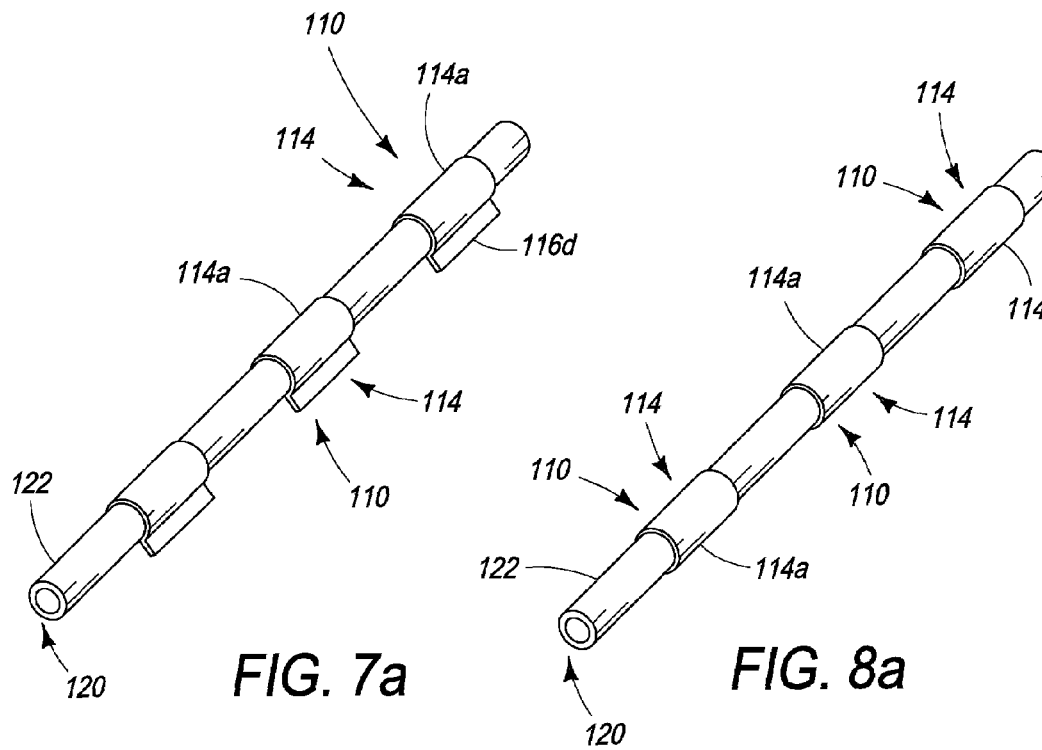
FIG. 7a
FIG. 8a
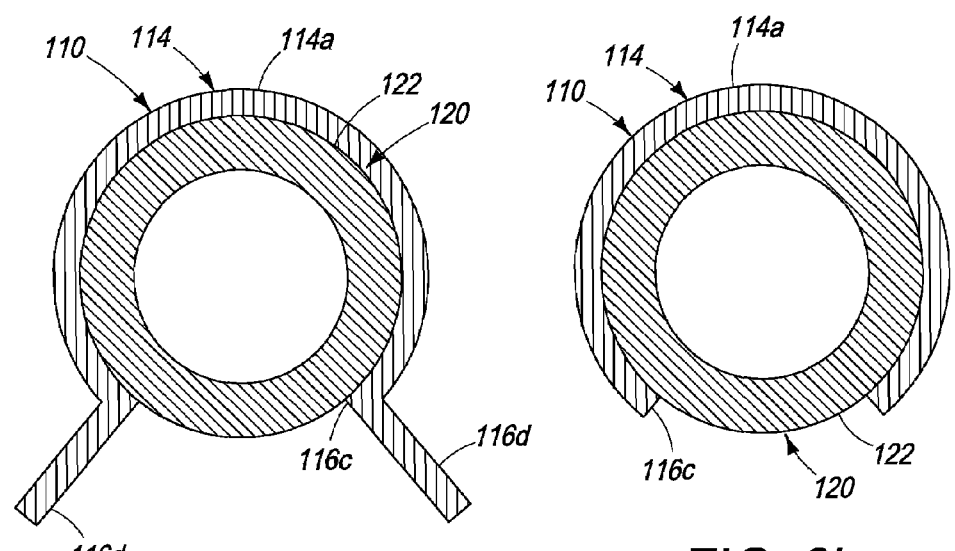
FIG. 7b
FIG. 8b

US 7,374,318 B2

LIGHTED TUBING

BACKGROUND

The present invention relates to tubing, and more particularly to lighted tubing.

As known to those skilled in the art, medical tubing is commonly used in hospitals and medical settings. There are many accidents every year caused by patients, medical personnel, and visitors tripping over or otherwise dislodging undetected tubing at night. There are also documented deaths that have resulted from disconnected tubing and tubing that has been connected incorrectly. These accidents are unnecessary and unacceptable. At the same time, there are definitely problems with lighting the entire environment at night; patients often need rest, and many people are incapable of obtaining good rest in lit surroundings.

SUMMARY

Lighted tubing and methods of securing medical tubing are disclosed herein. Lighted tubing of one embodiment includes an elongate wall defining an interior channel and a light source attached to the wall.

In an embodiment, lighted tubing for medical use is provided, including an elongate wall defining an interior channel for transporting a substance and a light source attached to the wall.

In an embodiment, lighted tubing for medical use is provided, including an elongate wall defining an interior channel for transporting a substance, a luminator, and a conductor adjacent to and extending from the luminator to conduct light produced by the luminator along the wall.

In an embodiment, a method of securing medical tubing is provided. The method includes the steps of providing medical tubing, providing a light source, attaching the light source to an elongate wall of the medical tubing, and the light source indicating the location of the wall in a dark environment. The elongate wall defines an interior channel for transporting a substance.

BRIEF DESCRIPTION OF THE DRAWINGS

FIG. 7a shows a piece of lighted tubing in accord with an embodiment.

FIG. 7b shows a sectional view of the piece of lighted tubing of FIG. 7a.

FIG. 8a shows a piece of lighted tubing in accord with an embodiment.

FIG. 8b shows a sectional view of the piece of lighted tubing of FIG. 8a.

DETAILED DESCRIPTION

Figure 1:
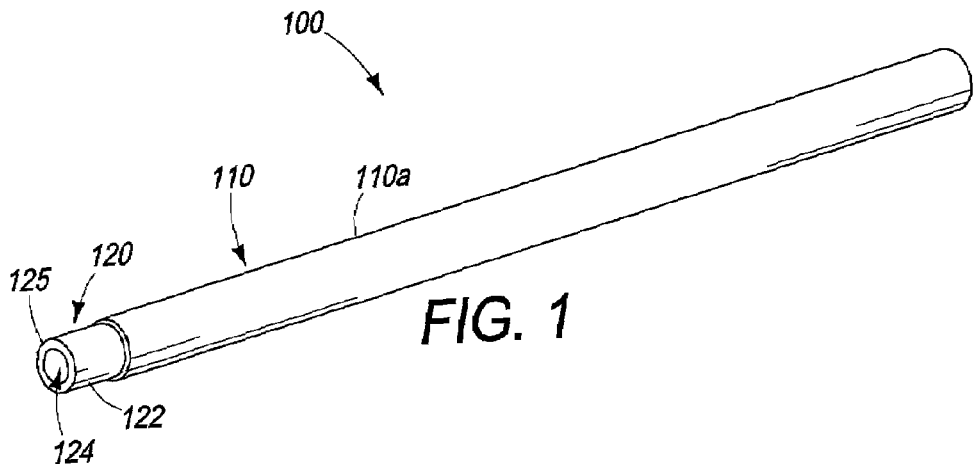
FIGS. 1 through 4 show pieces of lighted tubing in accord with various embodiments.

FIG. 1 shows a piece of lighted tubing 100 according to an embodiment. The lighted tubing 100 includes a light source 110 and tubing 120 having an elongate wall 122 defining an interior channel 124 for transporting a substance. The tubing 120 is preferably medical tubing, i.e., oxygen tubing. While the tubing 120 is not limited to oxygen tubing, the tubing 120 is preferably a highly inert and flexible sterile tubing for medical use. The tubing 120 may present a circular cross-section 125 or a cross-section 125 having another shape, such as oval or oblong, for example. The light source 110 allows the tubing 120 to be seen in the dark, preventing accidents caused by tripping over, dislodging, or completely disconnecting unlit tubing 120.

The light source 110 is shown in FIG. 1 as a chemical coating 110a having glow-in-the-dark characteristics. Numerous phosphorescent paints 110a found in the marketplace today would be appropriate. After exposure to incident radiation (light), some of these coatings 110a may emit light for up to twelve hours that can be seen by humans. Further, according to their manufacturers, some of these phosphorescent paints 110a can be charged millions of times and have a lifespan of over twenty years. These coatings 110a can be obtained in various colors, and may be nearly transparent in lit surroundings.

Figure 2:
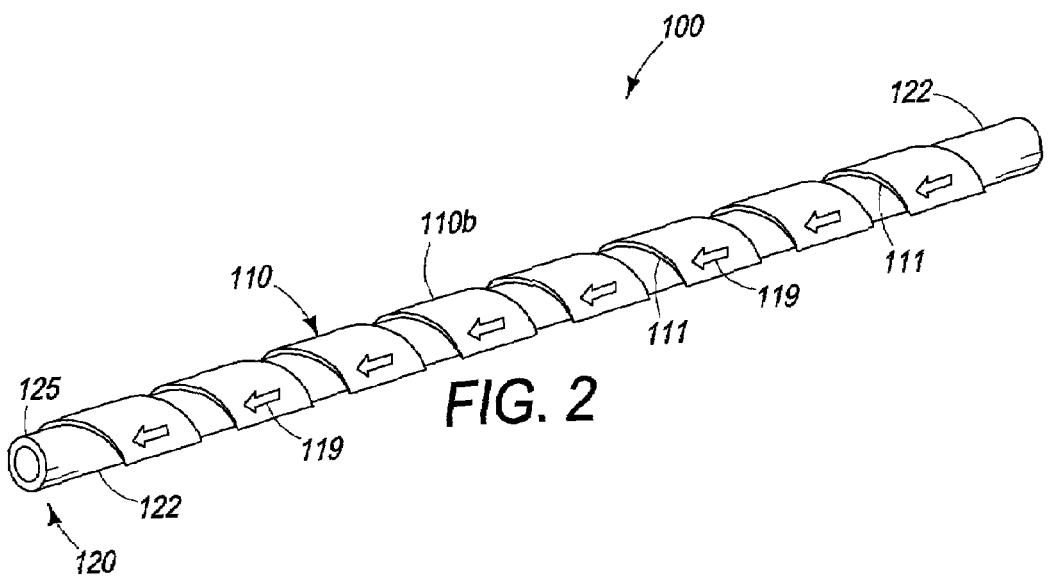
Figure 3:
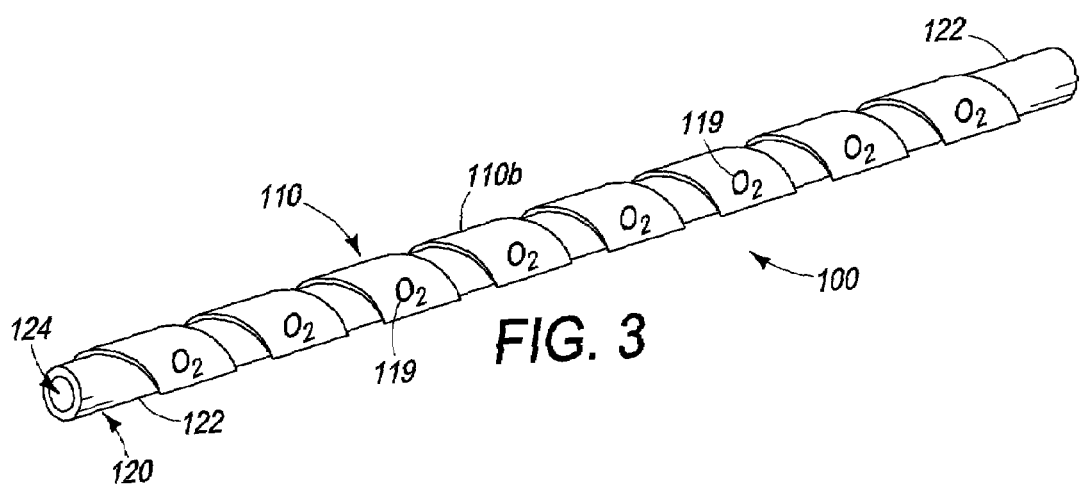

As shown in FIGS. 2 and 3, the light source 110 may include a piece of tape 110b having glow-in-the-dark characteristics. The tape 110b may have adhesive 111 attaching the tape 110b to the wall 122 (FIG. 2), or the tape may be a vinyl tape 110b capable of being selectively affixed to the wall 122 through an electrostatic interaction (FIG. 3). If the tape 110b includes the adhesive 111, the tape 110b may be constructed of any of a variety of materials, including cloth, plastic, metal, paper, and others. The tape 110b may be manufactured from a material having glow-in-the-dark characteristics, or glow-in-the-dark characteristics may be added to the tape 110b, such as by adding the chemical coating 110a discussed above to the tape 110b.

Figure 4:
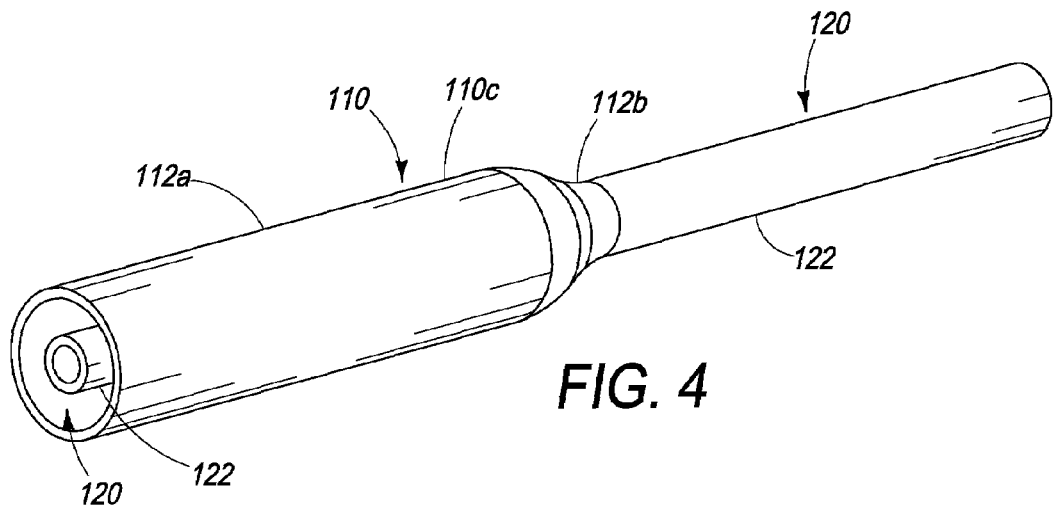

As shown in FIG. 4, the light source 110 may include a heat-shrink material 110c having glow-in-the-dark characteristics. Somewhat similar heat-shrink materials are currently used with electrical cords. The heat-shrink material may be manufactured from a material having glow-in-the-dark characteristics, or glow-in-the-dark characteristics may be added to the heat-shrink material. Portion 112a represents the heat-shrink material 110c in an initial state, and portion 112b represents the heat-shrink material 110c after heat has been added.

Figure 5:
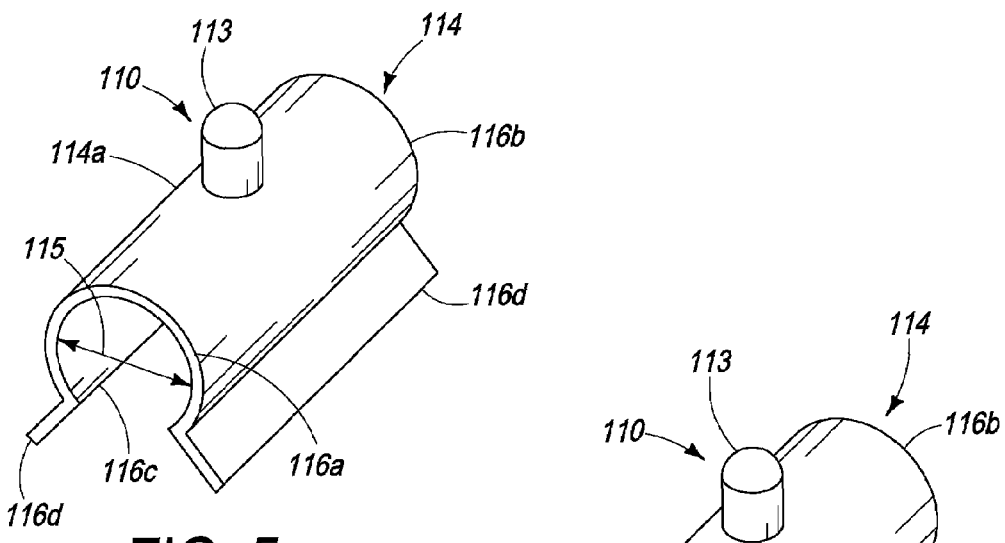
FIG. 5 shows a light source operatively connected to a clip in accord with an embodiment.
Figure 6:
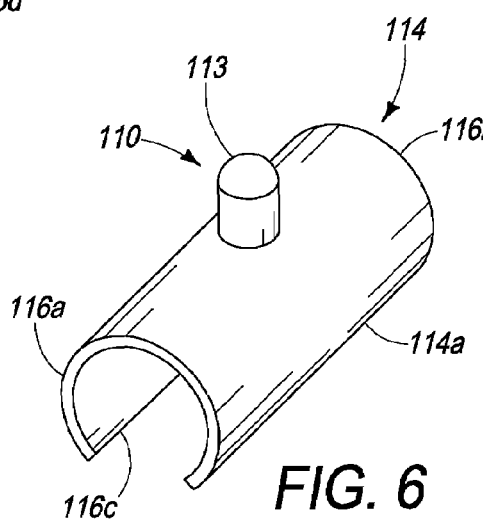
FIG. 6 shows the light source and clip of FIG. 5 without flanges.

FIGS. 5 and 6 show a light source 110 that includes a luminator 113, i.e., a LED or a light bulb. The ruminator 113 is preferably a LED due to the negligible amount of heat produced by a LED, though other luminators 113 may be used. The luminator 113 is operatively connected to a clip 114. The clip 114 shown in FIGS. 5 through 9 is a sleeve 114a having an inner diameter 115 that is larger than an outer diameter of the elongate wall 122. The sleeve 114a presents first and second ends 116a, 116b, and an opening 116c extends from the first end 116a to the second end 116b to allow the sleeve 114a to be selectively positioned about the wall 122, as shown in FIGS. 7a through 8b. As shown in FIGS. 5, 7a, and 7b, the sleeve 114a may include a respective flange 116d extending outwardly from each side of the sleeve opening 116c so that a user may easily enlargen the sleeve opening 116c and selectively position the sleeve 114a about the wall 122. Though not shown, the luminator 113 is in communication with a power source (i.e., a battery). Also, the ruminator 113 may be constantly emitting light, or a user interface (i.e., a switch) may be in communication with the luminator 113 to allow the ruminator 113 to selectively emit light.

FIGS. 7a through 8b show a light source 110 without a ruminator 113. Instead, the sleeve 114a includes glow-in-the-dark characteristics. The sleeve 114a may be manufactured from a material having glow-in-the-dark characteristics, or glow-in-the-dark characteristics may be added to the sleeve 114a, such as by adding the chemical coating 110a discussed above to the sleeve 114a. FIGS. 7a and 8a show that a plurality of sleeves 114a may be operatively attached to the wall 122. The sleeves 114a may be positioned periodically along substantially the entire length of the wall 122 so the location of the entire wall 122 may be observed in the dark. Alternately, one or more sleeve 114a may be positioned along a predetermined portion of the wall 122 so that the predetermined portion may be observed in the dark.

Figure 9:
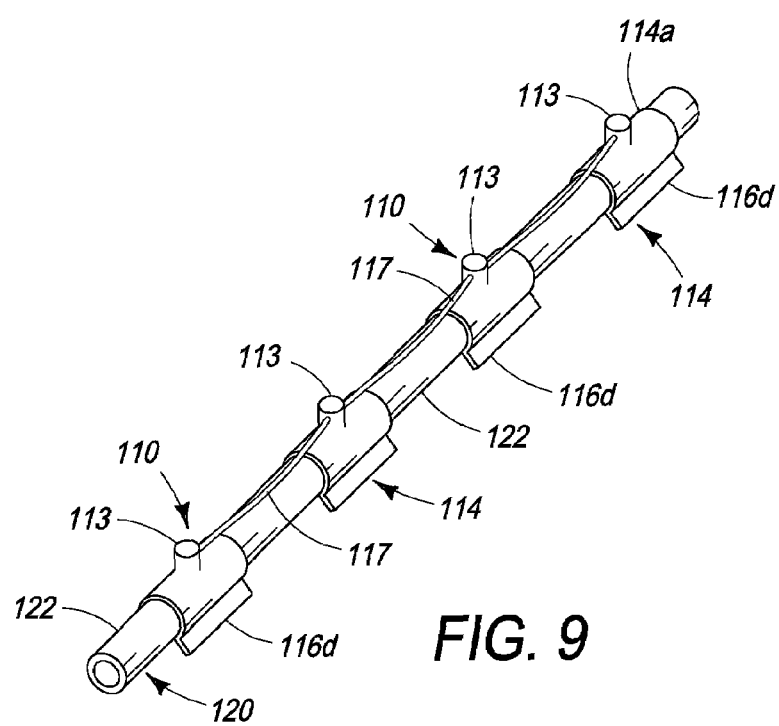

FIG. 9 shows a light source 110 that includes a ruminator 113. A conductor 117 preferably conducts light produced by the ruminator 113, further marking the position of the wall 122. The conductor 117 may also connect the luminators 113 to one another, forming a chain of luminators 113. The conductor 117 is preferably flexible and may be constructed of a fiberoptic bundle.

Figure 10:
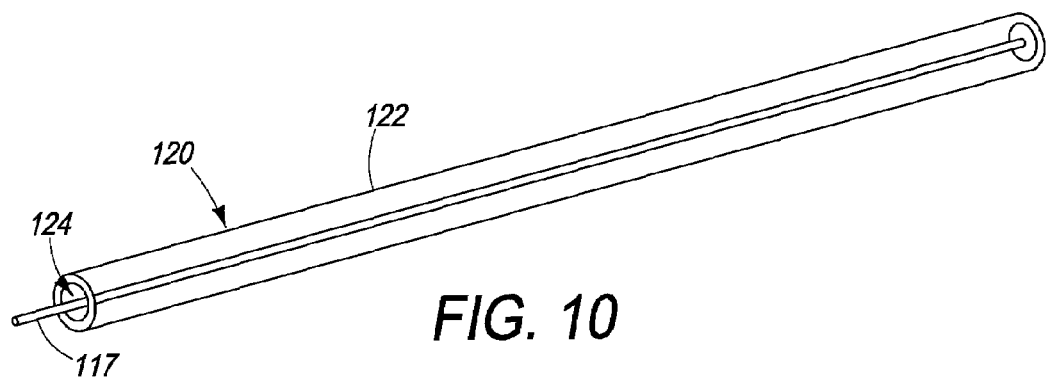
FIGS. 9 through 12 show pieces of lighted tubing in accord with various embodiments.
Figure 11:
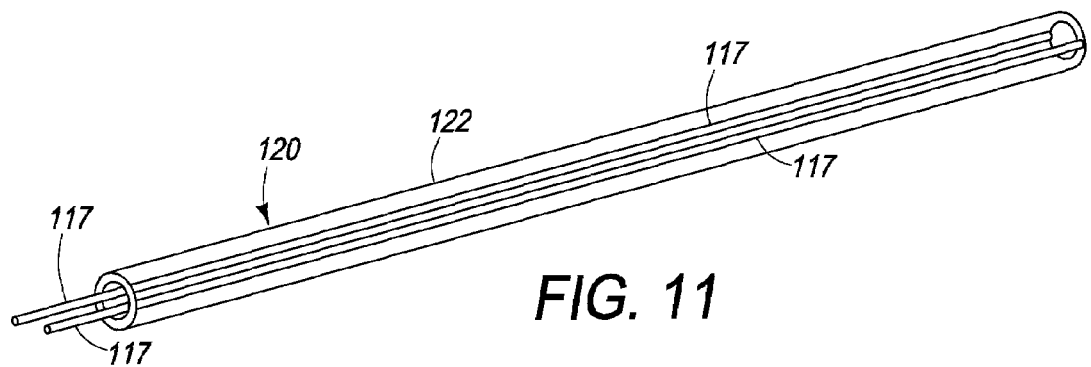

FIGS. 10 and 11 show a conductor 117 positioned inside the tubing interior channel 124 (FIG. 10) and positioned inside the tubing wall 122 (FIG. 11). A luminator 113 (not shown) introduces light into the conductors 117, and the conductors 117 conduct and transmit that light. This effectively displays the position of the wall 122.

Figure 12:
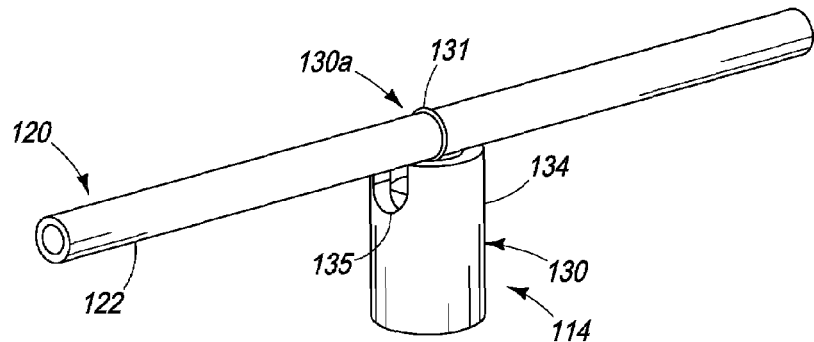
Figure 13:
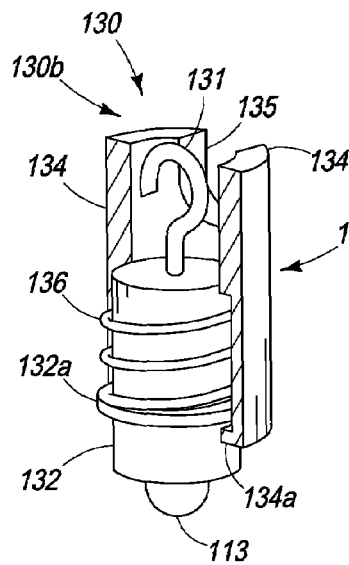
FIG. 13 shows a sectional view of the light source and clip of FIG. 12. The clip is shown in a closed configuration.
Figure 14:
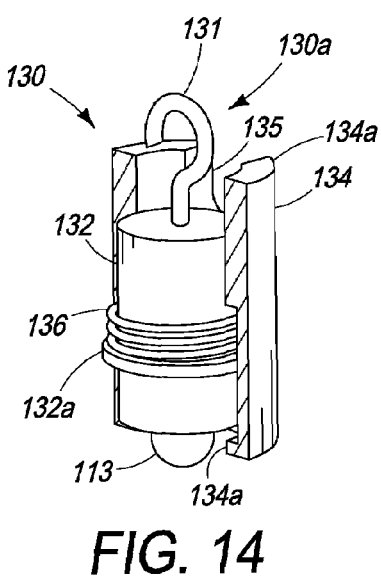
FIG. 14 shows a sectional view of the light source and clip of FIG. 12. The clip is shown in an open configuration.
Figure 15:
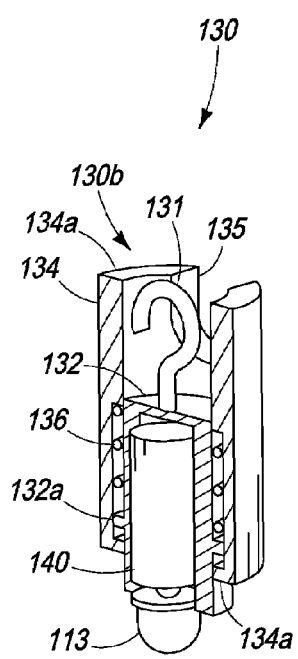
FIG. 15 shows a sectional view of the light source and clip of FIG. 12. The clip is shown in a closed configuration.

FIGS. 12 through 15 show a clip 114 that is a hook apparatus 130 for selectively attaching the luminator 113 to the wall 122. The hook apparatus 130 preferably houses a power source 140 (i.e., a battery) in communication with the luminator 113, and as seen in FIGS. 12 through 15, the luminator 113 may protrude from the hook apparatus 130. Alternately, the ruminator 113 may be located inside the hook apparatus 130 as long as the hook apparatus is transparent or includes openings to allow light from the luminator 113 to escape. The hook apparatus 130 may include inner and outer portions 132, 134 capable of sliding along one another to alter the hook apparatus 130 between an open configuration 130a (FIGS. 12 and 14) and a closed configuration 130b (FIGS. 13 and 15). A hook 131 may be attached to the inner portion 132 for selectively connecting the inner portion 132 to the wall 122. A biasing element 136 (i.e., a spring or tension cord) is preferably in communication with the inner and outer portions 132, 134 to bias the hook apparatus 130 toward the closed configuration 130b. The outer portion 134 may define a recessed region 135 adjacent a top end 134a so that the wall 122 may be located at least partially inside the hook apparatus 130 when the hook apparatus 130 is attached to the wall 122 and the hook apparatus 130 is at the closed configuration 130b. The inner and outer portions 132, 134 preferably include interfering protrusions 132a, 134a so that the inner and outer portions 132, 134 are restricted in their range of motion. The interaction between the protrusions 132a, 134a keeps the wall 122 from being kinked or damaged by the outer portion 134 or the hook 131.

An example of use for the hook apparatus 130 (FIGS. 12-15) is as follows. The hook apparatus 130 is initially at the closed configuration 130b (FIG. 13) due to the biasing element 136. Opposing ends of the inner and outer portions 132, 134 may be squeezed together, altering the hook apparatus 130 to the open configuration 130a (FIG. 14). The hook 131 may then be placed about the wall 122 (FIG. 12). By releasing the opposing ends of the inner and outer portions 132, 134, the hook apparatus 130 returns to the closed configuration 130b (FIG. 13) due to the biasing element 136, removably attaching the hook apparatus 130 to the wall 122.

As shown in FIGS. 2 and 3, the light source 110 may define indicia 119. The indicia 119 may provide information pertaining to the medical use of the tubing 120 (FIG. 3, for example), the direction of flow for a substance inside the tubing 120 (FIG. 2, for example), manufacturer information, or other relevant subjects. By indicating direction of flow, the indicia 119 also makes it very easy to observe and identify coils or kinks in the tubing 120. The indicia 119 may alternately provide comforting or emotionally-beneficial markings, such as teddy bears, snowflakes, etc. Such markings may be especially comforting to a child, though they are not solely intended for use with children. The indicia 119 as shown in FIGS. 2 and 3 may include the glow-in-the-dark characteristics discussed above, or the indicia 119 as shown in FIGS. 2 and 3 may be viewable because of a lack of glow-in-the-dark characteristics. Importantly, contrast between the characteristics of the indicia 119 and the surrounding area define the indicia 119. Though only shown in FIGS. 2 and 3, the indicia 119 can be used for any of the described embodiments. For embodiments incorporating luminators 113, a cover lens having indicia-defining light passageways may be placed adjacent the luminators 113 to define the indicia 119 with the light produced by the luminators 113.

What is claimed is:

1. Lighted tubing, comprising:
   an elongate wall defining an interior channel for transporting a substance, the elongate wall having first and second ends and a central portion therebetween;
   a light source attached to an outer surface of the wall, the light source indicating the location of the wall central portion in a dark environment;
   a power source; and
   a hook apparatus having inner and outer portions movable between open and closed configurations, the hook apparatus housing the power source;
   wherein a biasing element is in communication with the inner and outer portions to bias the inner and outer portions toward the closed configuration; and
   wherein the hook apparatus has a hook attached to the inner portion for removably attaching the light source to the wall, the hook apparatus being removable from the wall only when the inner and outer portions are at the open configuration.

2. The lighted tubing of claim 1, wherein:
   the outer portion defines a recessed region adjacent a top end of the outer portion; and
   the wall is at least partially inside the recessed region when the hook is attached to the wall and the inner and outer portions are at the closed configuration.

3. The lighted tubing of claim 2, wherein the inner and outer portions include protrusions that restrict the range of motion between the inner and outer portions to prevent damage to the wall.

4. The lighted tubing of claim 3, wherein the tubing is medical tubing.

5. The lighted tubing of claim 3, wherein the light source defines indicia.

6. The lighted tubing of claim 3, wherein the light source protrudes from the hook apparatus.

7. The lighted tubing of claim 3, wherein the light source is located. inside the hook apparatus.

8. The lighted tubing of claim 1, wherein the inner and outer portions include protrusions that restrict the range of motion between the inner and outer portions to prevent damage to the wall.

9. The lighted tubing of claim 8, wherein the light source protrudes from the hook apparatus.

10. The lighted tubing of claim 8, wherein the light source is located inside the hook apparatus.

11. The lighted tubing of claim 8, wherein the light source defines indicia.

12. The lighted tubing of claim 1, wherein the light source protrudes from the hook apparatus.

13. The lighted tubing of claim 1, wherein the light source is located inside the hook apparatus.

14. The lighted tubing of claim 1, wherein the light source defines indicia.

15. The lighted tubing of claim 1, wherein the tubing is medical tubing.

16. Lighted tubing for medical use, comprising:
an elongate wall defining an interior channel for transporting a substance, the elongate wall having first and second ends and a central portion therebetween; and
a light source attached to an outer surface of the wall, the light source indicating the location of the wall central portion in a dark environment;
wherein the light source includes a LED in communication with a power source;
wherein a hook apparatus having inner and outer portions movable between open and closed configurations houses the power source;
wherein a biasing element is in communication with the inner and outer portions to bias the inner and outer portions toward the closed configuration; and
wherein the hook apparatus has a hook attached to the inner portion for removably attaching the LED to the wall.

17. The lighted tubing as in claim 16, wherein the light source defines indicia providing information pertaining to the medical use.

18. The lighted tubing as in claim 16, wherein the light source defines indicia displaying a direction of flow for the substance.

19. The lighted tubing as in claim 16, wherein:
the outer portion defines a recessed region adjacent a top end of the outer portion; and
the wall is at least partially inside the recessed region when the hook is attached to the wall and the inner and outer portions are at the closed configuration.

20. The lighted tubing as in claim 16, wherein the inner and outer portions include protrusions that restrict the range of motion between the inner and outer portions to prevent damage to the wall.

21. The lighted tubing of claim 16, wherein the light source defines indicia.

22. Lighted tubing for medical use, comprising:
an elongate wall defining an interior channel for transporting a substance;
a hook apparatus having:
inner and outer portions movable between open and closed configurations;
a biasing element in communication with the inner and outer portions to bias the inner and outer portions toward the closed configuration; and
a hook attached to the inner portion for removable attachment to the wall; and
a light source coupled to the hook apparatus;
wherein the outer portion defines a recessed region adjacent a top end of the outer portion; and
wherein the wall is at least partially inside the recessed region when the hook is attached to the wall and the inner and outer portions are at the closed configuration.

23. The lighted tubing as in claim 22, wherein the inner and outer portions include protrusions that restrict the range of motion between the inner and outer portions to prevent damage to the wall.

24. The lighted tubing of claim 22, wherein the light source protrudes from the hook apparatus.

25. The lighted tubing of claim 22, wherein the light source is located inside the hook apparatus.

26. The lighted tubing of claim 22, wherein the light source defines indicia.

* * * * *